(12) United States Patent  
Smith

(10) Patent No.: US 6,249,645 B1
(45) Date of Patent: Jun. 19, 2001

(54) POTPOURRI KETTLE THAT IS ADAPTED FOR USE IN A VEHICLE

(76) Inventor: Tamu Smith, 441 N. 2530 West, Provo, UT (US) 84601

( * ) Notice: Subject to any disclaimer, the term of this patent is extended or adjusted under 35 U.S.C. 154(b) by 0 days.

(21) Appl. No.: 09/665,725

(22) Filed: Sep. 20, 2000

(51) Int. Cl.$^7$ .......................... A61H 33/12; A61M 16/00
(52) U.S. Cl. ............................................. 392/403; 392/390
(58) Field of Search .................... 392/390, 392, 392/394, 395, 403, 404, 405, 406; 219/202

(56) References Cited

U.S. PATENT DOCUMENTS

| | | | |
|---|---|---|---|
| D. 314,044 | * 1/1991 | Montanari | D23/366 |
| 3,006,042 | * 10/1961 | Calandra | 392/390 |
| 5,373,581 | 12/1994 | Smith . | |
| 5,394,506 | * 2/1995 | Stein et al. | 392/390 |
| 5,647,052 | 7/1997 | Patel et al. . | |
| 5,710,406 | * 1/1998 | Garris et al. | 392/390 |
| 5,788,931 | * 8/1998 | Quintana | 392/390 |
| 5,903,710 | 5/1999 | Wefler et al. . | |
| 5,945,094 | 8/1999 | Martin et al. . | |
| 5,976,503 | 11/1999 | Martin et al. . | |
| 6,085,027 | * 7/2000 | Sexton | 392/390 |
| 6,099,137 | * 8/2000 | McCormack et al. | 392/390 |

FOREIGN PATENT DOCUMENTS

0123456 A2 * 1/2000 (EP) ..................................... 100/100

* cited by examiner

*Primary Examiner*—Sang Paik
(74) *Attorney, Agent, or Firm*—Thorpe North & Western

(57) ABSTRACT

There is a scent device that is adapted for use in a vehicle. Particularly, there is a bowl having a heater element adapted for use in a vehicle, the bowl being suitable for use with various types of scent supplies that are not otherwise usable in vehicle air fresheners. Uniquely, there is a potpourri container for vehicle operation, that has a heater element, and a bowl, thermally coupled to the heater element, including at least one cavity and preferably more than one cavity, designed to hold a plurality of scents, and a quantity of solution. Additionally, there is a cover, positioned over the bowl to seal the cavity, having a sunken section, located centrally to the cover; pores, located through the cover to allow vapor to escape from the cavity; and a lip, positioned on a bottom side of the cover, designed to fit within the bowl and hold the bowl in place. Moreover, there is a handle used for easy removal of the bow.

11 Claims, 1 Drawing Sheet

POTPOURRI KETTLE THAT IS ADAPTED FOR USE IN A VEHICLE

THE FIELD OF THE INVENTION

The present invention relates generally to a scent device that is adapted for use in a vehicle. Particularly, there is a bowl having a heater element adapted for use in a vehicle, the bowl being suitable for use with various types of scent supplies that are not otherwise usable in vehicle air fresheners.

BACKGROUND OF THE INVENTION

1. Description of the Related Art

There are a variety of scenting devices that are designed to freshen or give fragrance to the air in vehicles. For example, hanging air fresheners are frequently seen dangling from vehicle rear-view mirrors or car cigarette lighters. Sprays and mists are likewise often used to freshen the air inside a vehicle. Additionally, some air fresheners are plugged into a vehicle's cigarette lighter outlet whereby a volatile fragrance is emitted upon heating.

Potpourri kettles are used as a scenting device. Potpourri kettles are used to brew mixtures or solutions of flower petals and spices in a small amount of liquid. Sometimes the kettles are used to heat crystals, fragrant oils or other volatile substances. Because potpourri contains primarily natural ingredients, the scent emitted is very natural smelling and uniquely rich.

2. Related Art to the Present Invention

Examples of patents related to the present invention, each of which are herein incorporated by reference for their supporting teachings, are as follows:

U.S. Pat. No. 5,976,503 by Martin, et al. discloses an air freshener dispenser device comprising (1) a disposable air freshener cartridge, and (2) a disposable electrical plug housing. The cartridge has an elongated thermoplastic hollow body configuration with a sealed internal reservoir chamber of liquid air freshener medium, and the upper section of the cartridge body is shaped to a flat shallow extension of the cartridge chamber. An electrical-resistance heating element is affixed on the inner surface of the cartridge chamber shallow extension. A thin wick matrix extends internally from the cartridge chamber bottom up to the top of the chamber shallow extension. The cartridge has an integrally structured means adapted for removal of a top portion of the cartridge chamber shallow extension to expose an upper section of wick matrix to the atmosphere. The electrical plug housing is detachably secured and positioned proximate to the cartridge heating element. Activation of the heating element promotes air freshener dispersion into the atmosphere from the exposed wick.

U.S. Pat. No. 5,945,094 by Martin, et al discloses a disposable air freshener dispenser device which is adapted for engagement and support by a wall electrical outlet. The dispenser device consists of a cartridge which has a sealed content of liquid air freshener medium, and an absorbent matrix which can be exposed for wicking of air freshener into the atmosphere. An electrical-resistance type heater module is detachably secured and positioned proximate to the exposed absorbent matrix section for promotion of the wicking action.

U.S. Pat. No. 5,903,710 by Wefler, et al. discloses an air freshener dispenser device comprising (1) a disposable air freshener cartridge, (2) a disposable electrical plug housing, and (3) a reusable electrical plug for engaging a wall electrical outlet. The cartridge has an elongated thermoplastic hollow body configuration with a sealed internal reservoir chamber of liquid air freshener medium, and the upper section of the cartridge body is shaped to a flat shallow extension of the cartridge chamber. An electrical-resistance heating element is affixed on the inner surface of the cartridge chamber shallow extension. A thin wick matrix extends internally from the cartridge chamber bottom up to the top of the chamber shallow extension. The cartridge has an integrally structured means adapted for removal of a top portion of the cartridge chamber shallow extension to expose an upper section of wick matrix to the atmosphere. The disposable electrical plug housing is detachably secured and positioned in front of the cartridge and proximate to the cartridge heating element. The plug housing has two short metal blades which extend through the cartridge vertical slots and engage the reusable electrical plug for conduction of an electrical current to the cartridge heating element, and for heat-promotion of air freshener wicking into the atmosphere.

U.S. Pat. No. 5,647,052 by Patel, et al. discloses a volatile substance dispenser which provides an indication of the dissipation of a quantity of volatile substance by changing an electrical signal level after a time duration corresponding to an expected period time for the quantity of volatile substance to disseminate. A heat source causes the volatile substance to disseminate into the atmosphere. Dissipation of the volatile substance is indicated. For example, dissipation may be indicated by a light bulb burning out where the light bulb is a limited duration bulb with a lifetime that corresponds to the quantity of volatile substance. The dispenser may be disposable and may also serve as a night light.

U.S. Pat. No. 5,373,581 by Smith discloses an automobile plug-in air freshener with a main body portion in a cylindrical configuration having an open outboard end and a closed inboard end and plugable into an electrical cigarette lighter socket of a vehicle. An extension portion has a cone shaped interior component rotatably positioned outwardly of the open end of the cylinder with an interior edge in a cylindrical configuration positioned rotatably in the outboard end of the main body portion with an exterior component in a rectangular configuration constituting a housing with an opened inboard end and louvers at the outboard end and a slot along an upper intermediate extent. A generally planar refill container in a rectangular configuration is removably positionable within the slot of the rectangular housing, the refill container having a fragrance therein activated by heat. A heating element is located within the main body portion adjacent to the outboard open end is energized by a switch actuated by rotation of the extension portion to heat the fragrance within the refill cartridge for disseminating a fragrance and freshening the adjacent air.

The foregoing patents reflect the state of the art of which the applicant is aware and are tendered with the view toward discharging applicant's acknowledged duty of candor in disclosing information that may be pertinent to the examination of this application. It is respectfully stipulated, however, that none of the patents teach or render obvious, singly or when considered in combination, applicant's claimed invention.

3. Problems with the Prior Art

Potpourri is typically made from flower petals, spices, crystals or oils. These substances are frequently brewed in a kettle either by themselves or mixed with a small amount of liquid. Since potpourri is typically either liquid or small particle size, its use is not practicable with present vehicle air-fresheners. The size and physical properties of potpourri necessitate a kettle of some sort. However, typical potpourri kettles are not adapted for use in a vehicle. Generally, potpourri kettles require a standard household plug in order to activate the heating element that vaporizes the potpourri mixture or solution. Furthermore, typical plug-in potpourri kettles are not well suited for use in a vehicle as they would be prone to spillage. Additionally, prior art air fresheners are not suitable for potpourri mixtures, which produce better scents. Moreover, potpourri pots are not situated for different people. Specifically, to change scents requires. What happens when two different people use the same vehicle, they would either have to use separate bowls or clean out the other potpourri out of the original bowl each time just to get their own scents placed therein.

SUMMARY OF THE INVENTION

There is a scent device that is adapted for use in a vehicle. Particularly, there is a bowl having a heater element adapted for use in a vehicle, the bowl being suitable for use with various types of scent supplies that are not otherwise usable in vehicle air fresheners. Uniquely, there is a potpourri container for vehicle operation, that has a heater element, and a bowl, thermally coupled to the heater element, including a cavity, designed to hold a scent supply, and a quantity of solution. Additionally, there is a cover, positioned over the bowl to seal the cavity, having a sunken section, located centrally to the cover; pores, located through the cover to allow vapor to escape from the cavity; and a lip, positioned on a bottom side of the cover, designed to fit within the bowl and hold the bowl in place. Moreover, there is a handle used for easy removal of the bow.

BRIEF DESCRIPTION OF THE DRAWINGS

These and other features of the invention can best be understood by the following description of the accompanying drawing as follows.

Figure 1:
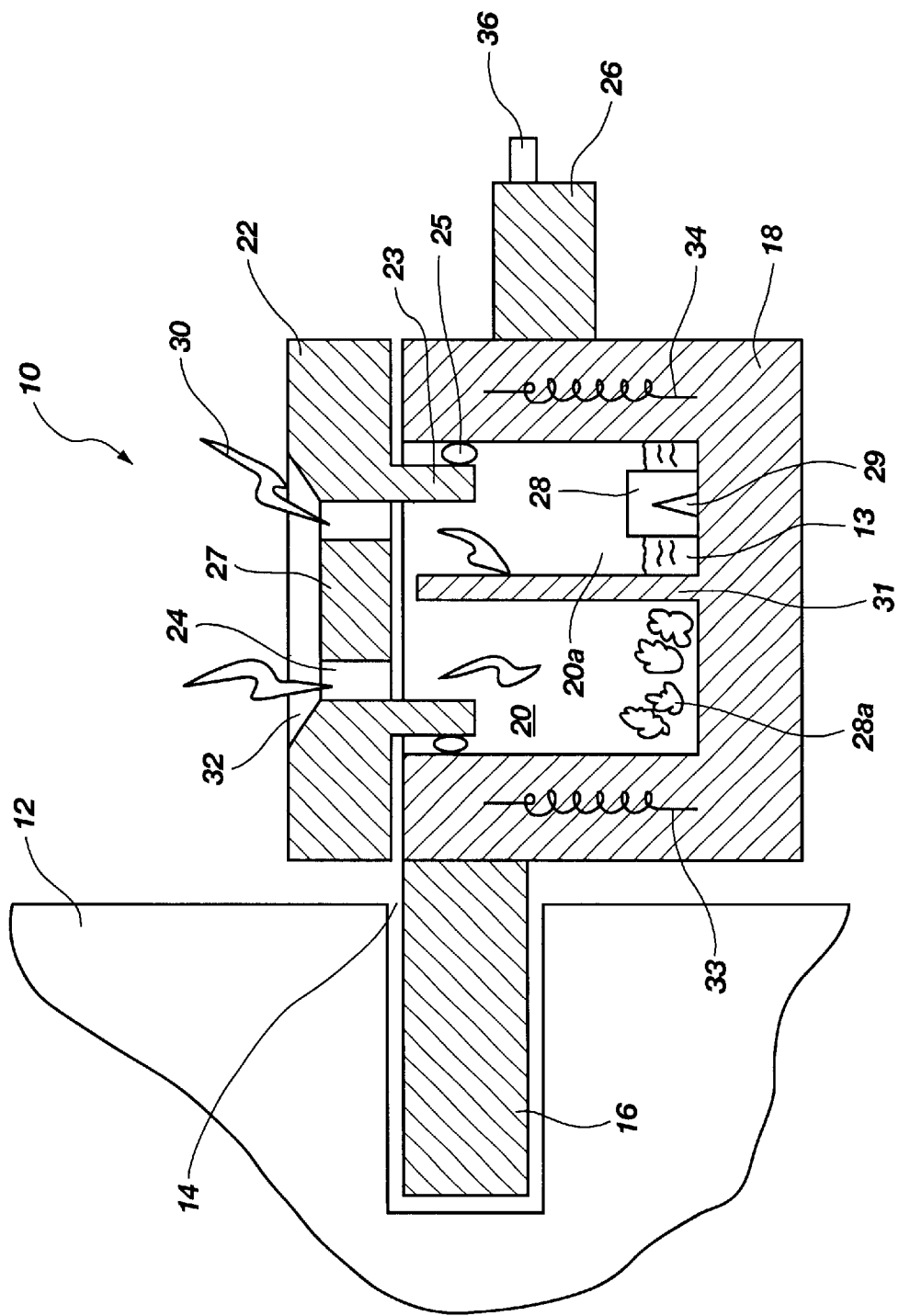
FIG. 1 is a cross-sectional schematic of the preferred embodiment.

It is noted that the drawings of the invention are not so scale. The drawings are merely schematic representations, not intended to portray specific parameters of the invention. The drawings are intended to depict only selected embodiments of the invention, and therefore should not be considered to be limiting the scope of the invention. The invention will be described with additional specificity and detail through the use of the accompanying drawings. Like numbering between figures represent like elements.

DETAILED DESCRIPTION OF THE PREFERRED EMBODIMENT

Referring to FIG. 1, there is a scent device 10 adapted for use in a vehicle. In particular, the scent device is made up of a bowl 18, coupled to a heater element 16. The heater element 16 is adapted for use in a cigarette lighter outlet 14 in a vehicle dash 12. The bowl 18 comprises a cavity 20 wherein a scent supply 28 is placed in a quantity of solution or mixture 13. In the preferred embodiment, a cover 22 is placed over the top of the bowl 18, where a sunken bowl section 27 is located as illustrated in a centrally placed location. The cover 22 has centrally located pores 24 that allow the vapor of scent 30 to be released into the vehicle. The cover 22 also has a lip 23 surrounded by an o-ring 25. Additionally, the scent device 10 may have a handle 26 that allows one to hold the scent device 10 without being burned from the heated bowl 18. There is a recessed depression 32 at the top of cover 22 to allow any spilt fluid to drain back into the cavities 20 and 20a.

To accommodate wax based scents, like wick-less candles, a projection or holder 29 may be included. Wick-less candles do not need liquid or oil to liberate the scent from the scent carrying base material, in this case, wax. By heating the wax, the scent is liberated.

Additionally, to accommodate several potpourri scents, the cavity 20 is split by wall 31, which will create several cavities 20 and 20a. It is illustrated that potpourri leaves 28a are in cavity 20 and wax-less candle 28 and oil 13 are in cavity 20a. To deal with the several cavities, bowl section heating element 33, also referred to as a cavity heater, xx is places only near cavity 20 and bowl section heating element 34 is placed only near cavity 20a. Switch 36 is used to switch between cavities 20 and 20a, or the switch could activate both cavities if both cavities 20 and 20a hold the same type of scent to get double the output of vapors 30.

In operation, a skilled artisan of potpourri mixture and heating will understand that there are several advantages to the operation of the present invention. When the cover 22 is secured, the o-ring 25 is disposed against the inside wall of the bowl 18, thereby preventing the quantity of solution or mixture 13 from spilling out of the bowl 18. Upon activation of the heater element 16, and switch 36 is activated, for example, bowl section heating element 34 is activated, then cavity 20a will heat up, thus scent supply 28 and solution 13 will emit a vapor of scent 30 out of holes 24.

Remarks About the Preferred Embodiment

One of ordinary skill in the art of scent devices, and more particularly the art of scent devices adapted for use in a vehicle, will realize many advantages from using the preferred embodiment. First, the preferred embodiment provides a solution-tight or leak-proof container. This permits the user to choose from a variety of potpourri products that are not practicable with typical vehicle air-fresheners. For example, with the preferred embodiment, a user may release scent into his or her vehicle by brewing flower petals in a quantity of water or oil without spilling. The preferred embodiment also allows one to use potpourri crystals that melt. The fact that the pores 24 are off center of the cover adds the advantage that any spilt liquid will not reenter the bowl 20 at a location that would drip over the center of the scent supply 28. This is to ensure that there is no saturation of any given point of the scent supply that may cause burning if other areas were not saturated with liquid, which burning would cause unpleasant oders.

A further advantage exists in the cover. In the event of rough driving conditions, the cover 22 is designed with a sunken section 27 that aids in preventing the quantity of solution or mixture 13 from sloshing out or leaking over the sides of the cover 22. If any of the solution or mixture 13 escapes through the centrally located pores 24, the cover 22 will direct the solution or mixture 13 back down through the pores 24 and into the bowl 18.

Yet, another advantage of the preferred embodiment is that natural smells are created from brewed flower petals, spices, crystals, and oils. Many people prefer the natural scents and not the artificial scents created from distilled oils placed on fabric pads that are heated to liberate the scents. This uniquely rich and natural scent cannot be duplicated by typical vehicle air-fresheners found in the prior art.

Another advantage of the preferred embodiment is that it maximizes the scents a user may choose from. Since there are many varieties of potpourri and oils, the present invention allows the user to choose from a wide array of scents. The user is not required to buy a refill made by a particular manufacturer. This design also lets the user put several scents into the same pot 10, thus by simply setting the switch 36, the user can choose which scent they want to smell each time the user enters the car.

It is noted that heating elements 33 and 34 are merely representative of what actually would need to be designed for actual operation. The coils represent resistors that would have to be properly coupled to the lighter outlet 14 and switchably coupled to the switch 36 in a proper electrical way.

Variations of the Preferred Embodiment

One of ordinary skill in the art of making scent devices will realize that there are many different ways of accomplishing the preferred embodiment. For example, the bowl 18 in the present invention could be made of ceramic, metal or any material capable of being heated without substantial degradation. The shape of the bowl 18 could be square, oval or any non-round shape. The handle 26 may be made of, or coated with, a heat-resistant material and could be placed in most any usable location on the bowl 18. The heater element 16 could either cradle or encompass the entirety of the bowl 18 or have a wire running inside the bowl 18 wall. The cover 22 could be attached by a hinge or pivot mechanism to prevent loss. Additionally, the cover 22 could be secured in a closed position by means of a locking device, like a twist on cap.

Although the embodiment illustrates only two cavities 2 and 20*a*, it is contemplated to use any number of cavities. This will allow for even more than two choices of scents, say for example, ten or more with a larger bowl arrangement. The bowl compartments could be formed in a pie slice manner or a grid pattern of a two by five or three by three (nine total) type of arrangement.

Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function, manner of operation, assembly, and use may be made without departing from the principles and concepts set forth herein.

What is claimed is:

1. A scent liberating device for vehicle operation, comprising:
   a) a heater element (16);
   b) a bowl, thermally coupled to the heater element, including a leak-proof cavity, designed to hold a scent supply and a quantity of liquid solution without leaking;
   c) a cover (22), positioned over the bowl to seal the cavity, having:
      a sunken section (32), located centrally to the cover;
      a pore (24), located on the cover to allow vapor to escape from the cavity; and
      a lip (23), positioned on a bottom side of the cover, designed to fit within the bowl and hold the cover in place; and
   d) a handle (26).

2. The device of claim 1, wherein the heater element is designed to be located in a cigarette lighter outlet.

3. The device of claim 2, wherein the handle is located at a location opposite the heater element.

4. The device of claim 3, further comprising a resilient material positioned around the lip to both hold the cover in position and to prevent liquid from escaping from the bowl.

5. The device of claim 4, wherein the bowl further comprises a holder means, located in the cavity, for holding a scent supply.

6. The device of claim 5, further comprising a pivot mechanism to attach the cover to the bowl.

7. The device of claim 6, wherein the lip is a circular wall that extends into the bowl.

8. The device of claim 6, wherein the pore is located just off the center of the cover so any spilt liquid does not drip onto the center of the scent supply.

9. The device of claim 8, wherein there are more than one pores located just off center of the cover.

10. The device of claim 5, wherein the holder means comprises a pointed pin design that will mold the scent supply in position.

11. The device of claim 1, further comprising:
    a) a wall, positioned within the cavity to divide the cavity into a first and second cavity;
    b) a first and second cavity heater, where the first cavity heater is located next to the first cavity, and the second cavity heater is located next to the second cavity; and
    c) a switch that is electrically coupled to the first and second cavity heaters to control when the first and second cavity heaters are being operated.

\* \* \* \* \*